(12) United States Patent
Ralph et al.

(10) Patent No.: US 7,621,914 B2
(45) Date of Patent: Nov. 24, 2009

(54) ADJUSTABLE BONE PLATE

(75) Inventors: James D. Ralph, Seaside Park, NJ (US);
Thomas N. Troxell, Pottstown, PA (US);
Stephen L. Tatar, Montville, NJ (US)

(73) Assignee: BioDynamics, LLC, Englewood, NJ (US)

( * ) Notice: Subject to any disclaimer, the term of this patent is extended or adjusted under 35 U.S.C. 154(b) by 773 days.

(21) Appl. No.: 10/975,296

(22) Filed: Oct. 28, 2004

(65) Prior Publication Data

US 2006/0100625 A1    May 11, 2006

(51) Int. Cl.
*A61B 17/80* (2006.01)
(52) U.S. Cl. .................. 606/71; 606/280; 606/70
(58) Field of Classification Search .......... 606/69, 606/64, 68, 70–71, 280, 282
See application file for complete search history.

(56) References Cited

U.S. PATENT DOCUMENTS

| | | | |
|---|---|---|---|
| 5,993,449 A | 11/1999 | Schlapper et al. | |
| 6,106,527 A | 8/2000 | Wu et al. | |
| 6,136,002 A * | 10/2000 | Shih et al. | 606/250 |
| 6,623,486 B1 * | 9/2003 | Weaver et al. | 606/281 |
| 6,645,208 B2 | 11/2003 | Apfelbaum et al. | |
| 6,666,867 B2 | 12/2003 | Ralph et al. | |
| 6,689,134 B2 * | 2/2004 | Ralph et al. | 606/71 |
| 6,699,249 B2 | 3/2004 | Schlapfer et al. | |
| 6,872,210 B2 | 3/2005 | Hearn | |
| 7,128,744 B2 * | 10/2006 | Weaver et al. | 606/69 |
| 2003/0018335 A1 * | 1/2003 | Michelson | 606/61 |
| 2003/0153920 A1 * | 8/2003 | Ralph et al. | 606/71 |
| 2004/0019353 A1 * | 1/2004 | Freid et al. | 606/69 |
| 2004/0097925 A1 | 5/2004 | Boehm, Jr. et al. | |
| 2005/0004573 A1 * | 1/2005 | Abdou | 606/61 |
| 2005/0261688 A1 * | 11/2005 | Grady et al. | 606/69 |
| 2005/1026168 * | 11/2005 | Grady et al. | 606/69 |
| 2006/0235405 A1 * | 10/2006 | Hawkes | 606/69 |

FOREIGN PATENT DOCUMENTS

| | | |
|---|---|---|
| WO | WO 03/000148 A2 | 1/2003 |
| WO | WO 03/063714 A2 | 8/2003 |
| WO | WO 2004/062482 A2 | 7/2004 |

OTHER PUBLICATIONS

Extended European Search Report, Application No. EP 05 81 3057, Applicant: BioDynamics LLC, Jun. 9, 2009.*
International Search Report Oct. 24, 2005.

* cited by examiner

*Primary Examiner*—Eduardo C Robert
*Assistant Examiner*—Julianna N Harvey
(74) *Attorney, Agent, or Firm*—Norris McLaughlin & Marcus

(57) ABSTRACT

A longitudinally curved adjustable bone plate comprising a first plate having an end defined by at least two spaced prongs, and an end having means to fasten the plate to a body structure, e.g., the bone; and a second plate having an end defined by at least two straight bores for receiving the prongs, and an end having means to fasten the plate to a body structure, e.g., a bone; and a locking assembly for locking the prongs in the bores and fixing the overall length of the plate.

6 Claims, 7 Drawing Sheets

ADJUSTABLE BONE PLATE

FIELD OF THE INVENTION

The present invention relates to bone plates for holding body structures, such as the bones affixed relative to one another. More particularly this invention relates to longitudinal bone plate assemblies wherein the length of the plate is adjustable.

BACKGROUND OF THE INVENTION

Bone plates come in many sizes and shapes. The typical bone plate has a fixed dimension, and multiple holes for accommodating bone screws. In use, the surgeon brings together the fractured bone, places the bone plate atop the fracture, and inserts bone screws through the holes in the plate which overlie the healthy part of the bone, securing the bone about the fracture. Bone plates of many sizes are provided for the surgeon, and each is supplied with a number of holes so that the surgeon can arrange the plate over the fracture and have bone screw holes available above the healthy bone.

U.S. Pat. No. 6,666,867 describes a bone plate having an adjustable length. The adjustable length bone plate consists of a two parts, a first plate and a second plate, which are secured to the bone on opposite sides of the fracture. The first plate has laterally adjacent prongs which are inserted into the bore of a second plate. Bone screw holes are provided at the ends of the first and second plates to fasten them to the bone. The sliding bone plate has a locking mechanism, comprising a set screw passing through the second plate, and between the prongs of the first plate, fixing the length of the overall plate atop the fracture. The laterally adjacent prongs do not permit the surgeon to see the fracture surfaces coming together under the bone plate. Further, the use of only one locking screw permitted the assembled plate to twist longitudinally, permitting an unacceptable movement of the bone.

Orthopedic surgeons have also used DCP plates to stabilize fractured bone. The DCP plates also have openings for bone screws, and angulated openings, through which screws are "toed" into the bone, the tightening of the toed screws operating to move the bone, slightly, under the DCP plate. DCP plates have been used to move the bones on either side of the fracture closer together. This movement, however, was slight, and not easily controllable. Literally, the underlying bone is being pulled into place by the threads of a screw, providing no control over the twisting or turning of the bone, and the bending of the plate. In addition, the bone is pulled at an angle to the attached plates, resulting in a cocked bone, or an angle to longitudinal direction of the bone. This angulation, together with the micromotion in the bone, has lead to backing out of the screws.

It is an object of the invention to provide a two piece bone plate which is easy and inexpensive to manufacture.

It is a further object of the invention to provide a two piece bone plate which permits an observation window allowing the surgeon to see the bone surface coming together under the plate.

It is an object of the invention to provide a two piece bone plate which provides a strong locking mechanism for fixing the overall length of the plate, and resisting bending of the plate.

It is a further object of the invention to provide a bone plate which has an adjustable length, to permit the surgeon to fix the clinically effective length of the plate, permitting a better reconstruction or re-growth of bone at the fracture.

It is a further object of the present invention to provide a bone plate which resists bending, an thereby permits the surgeon better control of the movement of the underlying bone while adjusting the length of the plate.

It is still a further object of the present invention to provide a controlled method for bringing together the pieces of bone using a two piece bone plate, while controlling the turning of the bone.

SUMMARY OF THE INVENTION

These objects, as well as other objects which will become apparent from the discussion that follows, are achieved, in accordance with the present invention, which comprises a sliding bone plate assembly having an adjustable length and a longitudinal curvature. The sliding bone plate assembly comprises at least two plates, a first longitudinal plate, having at least two spaced longitudinal prongs at one end, and means for fastening the plate to a body structure at the other end; and a second longitudinal plate having at least two straight longitudinal bores at one end, each bore adapted for receiving one prong, and means for fastening the plate to a body structure at the other end. The means for fastening the plates to the body structure comprises a pair of threaded through holes adapted for receiving bone screws for making a fastening to the underlying bones.

The plates are constructed such that the prongs may be smoothly translated longitudinally within the straight bores to adjust the length of the plate assembly. The plate assembly further comprises a locking mechanism to fix the length of the overall plate assembly. The bores have an inner surface and the locking mechanism presses the prongs against the inner surface to fix the plates with respect to each other. The set screw forces the prongs against the respective inner surfaces of their bores.

In a preferred embodiment, the plate has two longitudinal prongs and two and two longitudinal bores, and the locking mechanism comprises a threaded bore in the second plate and a set screw passing between the prongs and into the threaded bore. In addition, both the first and second plates have a longitudinal curvature yielding a convex upper longitudinal surface and a concave lower longitudinal surface, and first and second plates have a lateral curvature yielding a convex upper lateral surface and a concave lower lateral surface.

The present invention further comprises a method of attaching at least two pieces of bone across a break, said method comprising placing the plate assembly over the break in the bone, such that the first longitudinal plate overlies the bone on one side of the break and the second longitudinal plate overlies the bone on the over side of the break; attaching the first longitudinal plate to the bone; moving the second longitudinal plate to translate the prongs out of the bores; and attaching the second longitudinal plate to the bone on the other side of the break, inserting the prongs of the first longitudinal plate into the bores of the second longitudinal plate, while observing the break through the window created by the spaced prongs, translate the prongs through the bores to bring together the two pieces of bone at the break, and locking the prongs in the bores to fix the length of the plate and position of the bones at the break.

For a full understanding of the present invention, reference should now be made to the following detailed description of the preferred embodiments of the invention as illustrated in the accompanying drawings.

DESCRIPTION OF THE PREFERRED EMBODIMENTS

Figure 1:
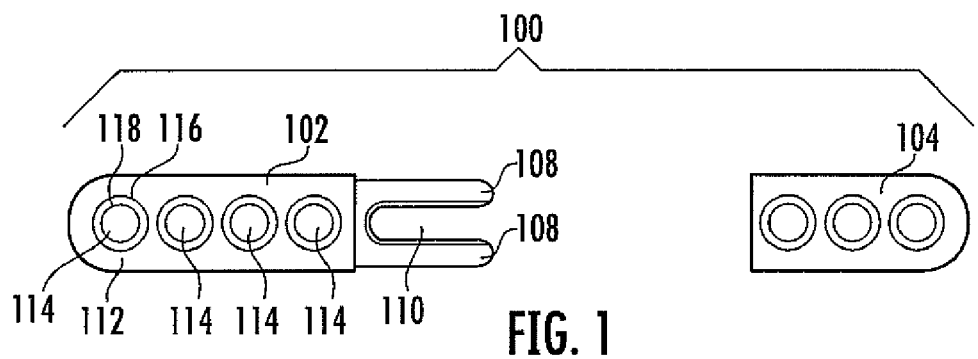
FIG. 1 is a top plane view of the sliding bone plate assembly of a preferred embodiment of the present invention.

The preferred embodiments of the present invention will now be described with reference to FIGS. 1-14 in of the drawings. Identical elements in the various Figures are designated with the same reference numerals.

As shown in FIG. 1 the sliding bone plate assembly, 100, of the present invention is comprised of a first longitudinal plate, 102, and a second longitudinal plate, 104. The first longitudinal plate has an end defined by at least two spaced prongs, 108. The spacing of the prongs permits an observation window, 110, between the prongs and the plates. As may be seen in FIG 1, the prongs 108 are located at the lateral edges of the plate to open up the window, 110.

The other end, 112, of the first longitudinal plate comprises means for fastening the plate to a body structure, such as, for example, a bone. In this particular embodiment the means comprises threaded through holes, 114, for receiving bone screws, not shown. The assembly may further include a bone screw having a shaft that can be inserted into the through hole and into a bone. The shaft can be threaded to cooperate with the threading in the through holes. The threading and shaft portion of the bone screws may be of a variety of standard designs, or a particular design which may be found more secure than the standard ones.

Figure 6:
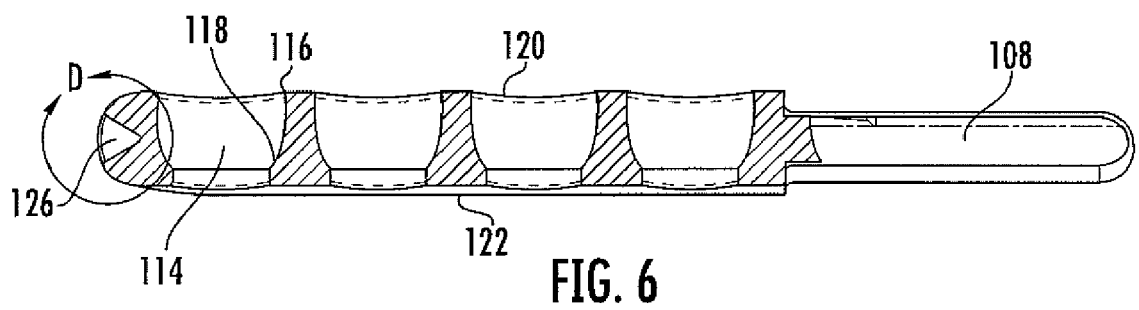
FIG. 6 is a cross-section of the first longitudinal bone plate 102 taken along lines 6-6 of FIG. 1.
Figure 6A:
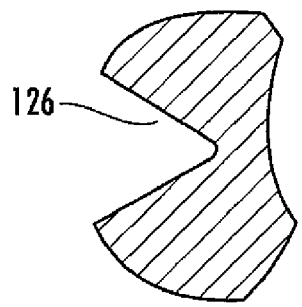
FIG. 6A is an enlarged view of detail D of FIG. 6.
Figure 6B:
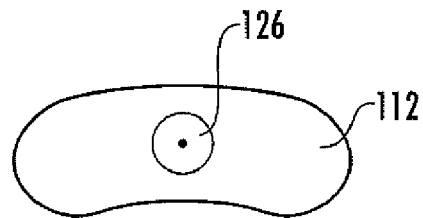
FIG. 6B is an end view of the longitudinal plate 102, illustrating the locking slot, 126, on end, 112, of the plate, 102
Figure 2:
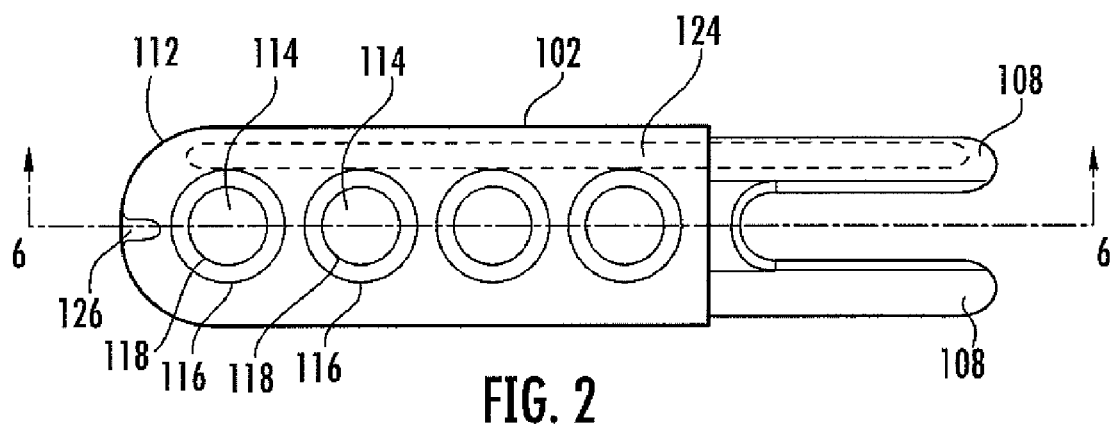
FIG. 2 is a top plan view of the first longitudinal bone plate 102 of FIG. 1.
Figure 3:
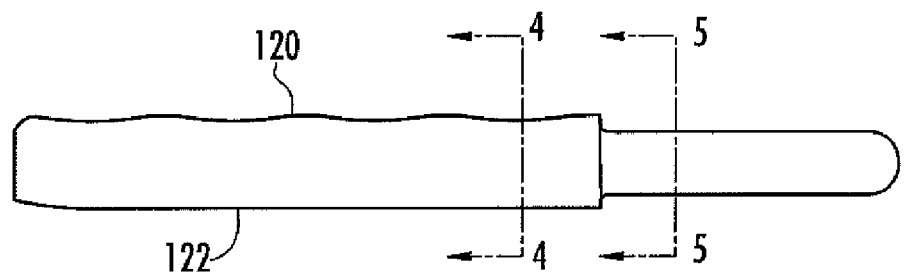
FIG. 3 is a side view of the longitudinal plate 104 of FIG. 2.
Figure 4:
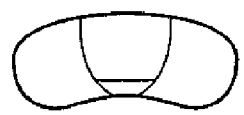
FIG. 4 is a cross section of the longitudinal plate 104 of FIG. 2 taken along lines 4-4.
Figure 5:
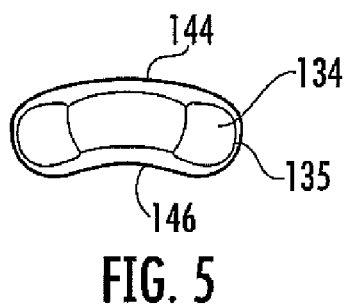
FIG. 5 is a cross section of the longitudinal plate 106 of FIG. 2 taken along lines 5-5.

As may best be seen in reference to FIGS. 2, 4 and 6, the holes, 114, for the bone screws include a recessed pocket having an upper edge, all 116, and a lower edge, 118. The recessed pocket contains the head of the bone screw, and any coupling therefore, such as disclosed in U.S. Pat. No. 4,689,134, so that neither protrudes from the surface of the bone plate to irritate the surrounding tissues.

Bone plates in general are constructed with both a longitudinal and lateral curvature so that the plates fit snugly against the curvature of the body structure. The first longitudinal plate, 102 has and upper longitudinally curved surface, 120, as well as a lower longitudinally curved surface, 122. The second longitudinal plate has similar upper longitudinally curved surface, 130, and lower longitudinally curved surface, 128, to lend an uninterrupted longitudinal curve to the sliding bone plate assembly.

As shown in FIG. 2 the prongs and plate of the first longitudinal plate may be reinforced, as by reinforcing rod, or tube, 124, which may be constructed of titanium, stainless steel, or other material to reinforce and strengthen the prong and/or plate.

Figure 7:
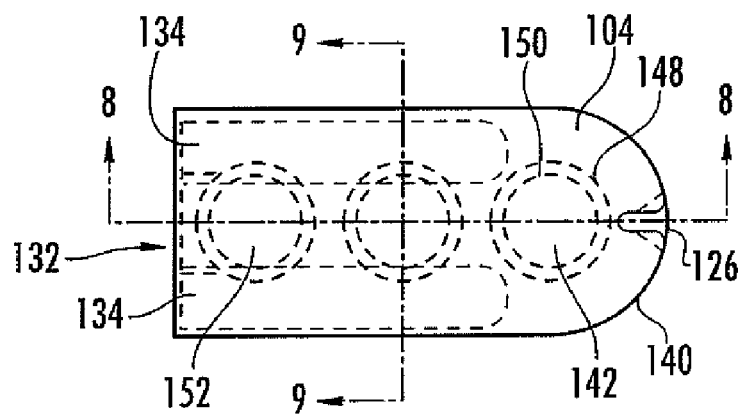
FIG. 7 is a top plane view in partial cross-section of the second longitudinal bone plate 104 of FIG. 1, with the prongs of the first longitudinal plate shown by dotted lines.
Figure 9:
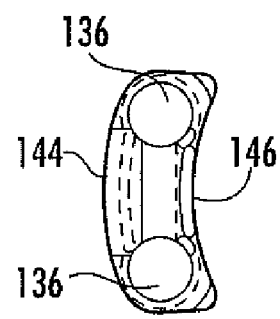
FIG. 9 is a partial cross-section of the prong plate of Figure seven taken along lines 9-9.

As illustrated in FIG. 7, the second longitudinal plate, 104, has an end, 132, defined by at least two straight prong bores, 134. These bores do not follow the longitudinal curvature of the second longitudinal plate, but begin near the lower surface of the second plate and rise towards the upper surface. The straight prong bores make the second longitudinal plate easier and less expensive to manufacture. The straight prong bores also make the first longitudinal plate easier and less expensive to manufacture, as the prongs need not have a longitudinal, or lengthwise, curvature. In addition the straight prong bores permit the prongs to be readily translated longitudinally through the bores, to adjust the length of the plate assembly At the other end, 140, of the second longitudinal plate 104, are means for fastening the plate to a body structure, such as, for example, bone. The means illustrated are holes, 142, which may be threaded, for receiving e.g. bone screws. Is preferred that the, 142, be recessed, as shown, the recessed beginning at the upper edge, 148, and curving to the lower edge 150, to form a pocket for receiving the head of the bone screw and any coupling means included therewith.

Figure 8:
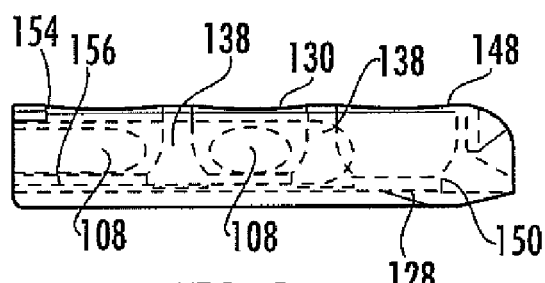
FIG. 8 is cross-sectional view of the sliding bone plate assembly pictured in FIG. 7, taken along lines 8-8, illustrating the prongs of plate 104 within the bores of the plate 104.

As may be seen in FIG. 8, the combination of the prong bores, 134, the recessed pockets for the bone screws, and the holes, 152, for set screws, to be described later, result in columnar structures, 138, which lend strength to the plate overall, and to the fastenings made by the bone screws and the set screws.

Located adjacent end, 132, of the second longitudinal plate, is a locking mechanism. In this embodiment, the locking mechanism comprises at least one threaded hole, 152, for a set screw. As shown, the threaded set screw hole, 152, is also recessed within a pocket defined by upper edge, 154, and lower edge, 156. As may be seen in FIG. 9, the prong bores, 134, have inner surfaces, 135. When the prongs are placed in the prong bores, and a set screw rotated into the threaded set screw hole, 152, the set screw separates the prongs presses against each prong and forces them against the inner surfaces 135, locking the prongs in the bores, and fixing the longitudinal length of the assembled bone plate. This fastening may be easily adjusted by backing out the set screw and readjusting the position of the prong in the bore. Preferably, the head of the set screw includes a recess that can be mated with a standard tool, such as a screw driver, to rotate the screw to fasten or readjust the fastening.

As shown in FIGS. 1, 6A, 6B, and 7, the ends of the plate are supplied with means such as the locking slots, 126, which may be engaged by closure means provided with plate assembly, to assist in moving of the plates together.

Into use, the surgeon places the assembled bone plate atop a fracture in the bone, to determine where the bone screws should be placed. Thereafter the surgeon may fasten one of the longitudinal plates to one side of the fracture, and then open up the plate assembly, moving the prongs out of the bores, and freeing the other plate. The other plate may then be placed atop the bone on the other side of the fracture and a bone screws or other means used to secure the plate to the bone. Thereafter the bone surfaces may be brought together by inserting the prongs in the prong bores, and moving that the two longitudinal plates together. During this process the surgeon may carefully observe the edges of the fracture coming together, by viewing the edges of the fracture through the observation window between the prongs.

Figure 10:
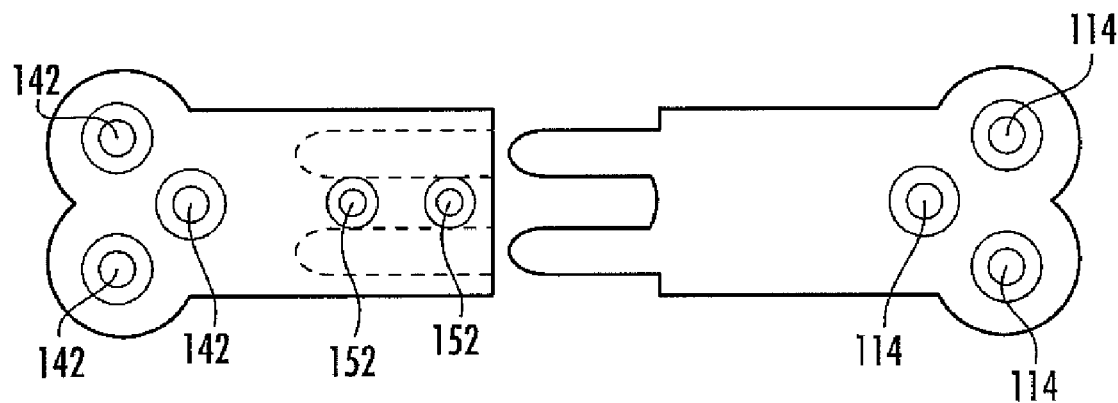
FIG. 10 is a top plan view of an alternative embodiment of the sliding bone plate according to the present invention.
Figure 11:
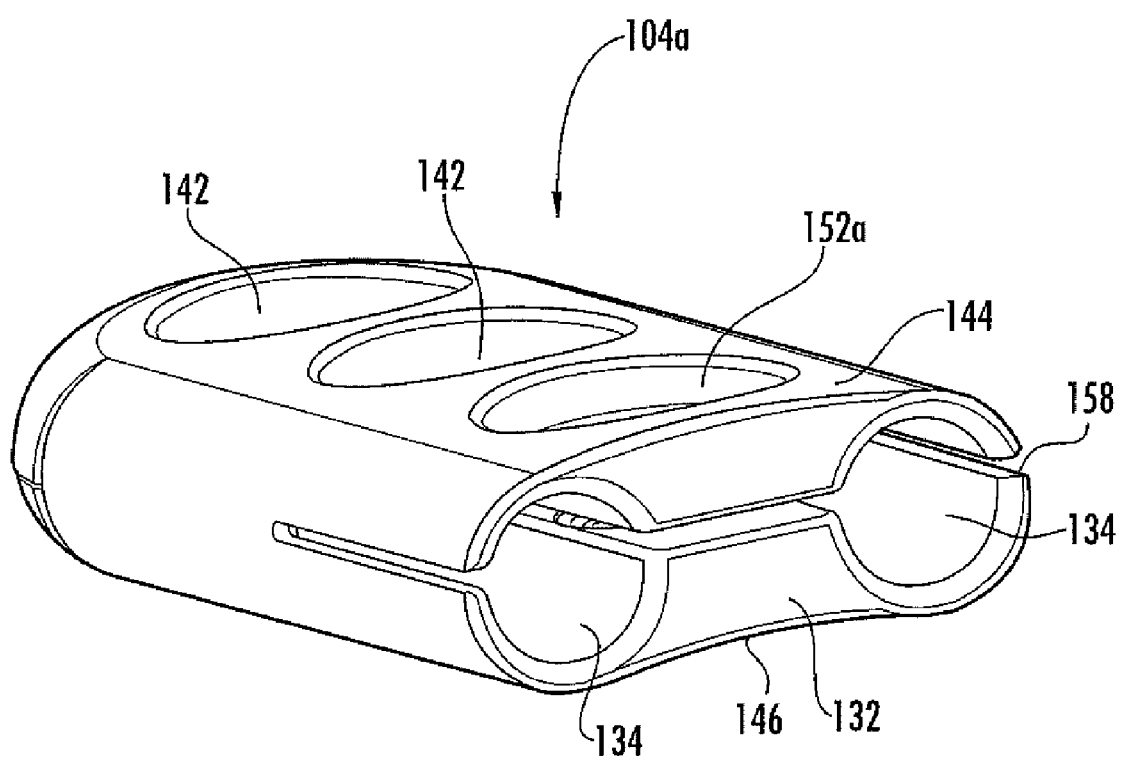
FIG. 11 is a top left perspective view of another embodiment of the second longitudinal bone plate of the present invention.

FIG. 10 illustrates an alternative embodiment of the sliding bone plate according to the present invention. In FIG. 10, the threaded holes, 114, in the first longitudinal plate are located at an angle to the longitudinal direction of the plate, and spaced wider apart from each other, by using a dog bone plate configuration. The threaded holes, 142, for the bone screws in the second longitudinal plate are similarly oriented. This configuration permits the surgeon to "toe" the bone screws at each end of the plate towards each other, to provide greater assurance that the bone screws will not pull out.

FIGS. 11 to 14 illustrate another preferred embodiment of the present invention. In this embodiment, the second longitudinal plate, 104a, has a slit, 158, carved into the end, 132. The slit extends through the midline of the plate from the end, 132 through the first set screw hole, 152a. As shown, this plate has only one set screw hole, 152a, however further set screw holes 152a may be included in a longer plate, and the slit, 158, will extend through the locking holes to the first bone screw hole from the end edge, 132.

Figure 12:
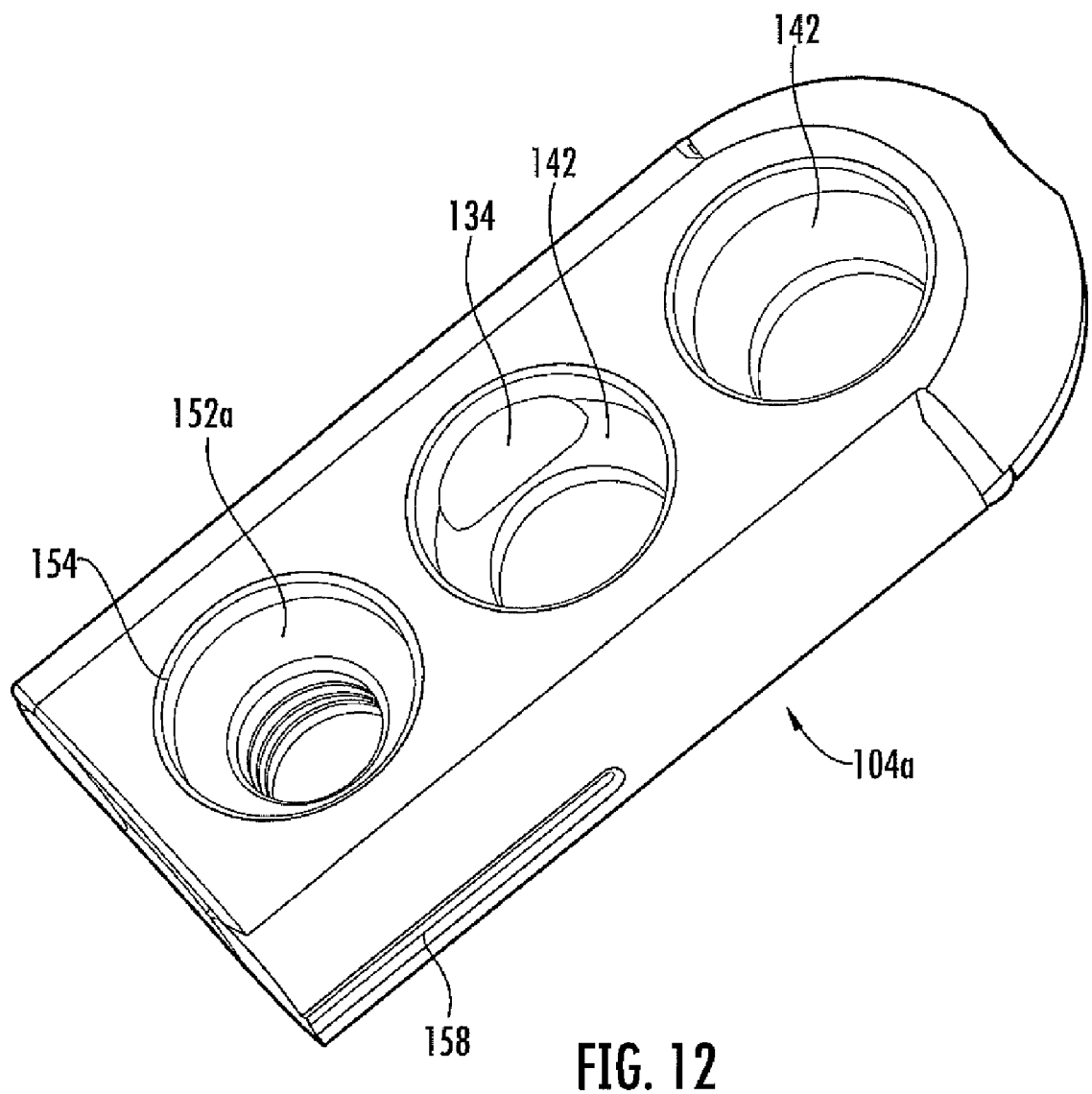
FIG. 12 is a top right perspective view of the plate of FIG. 11.
Figure 13:
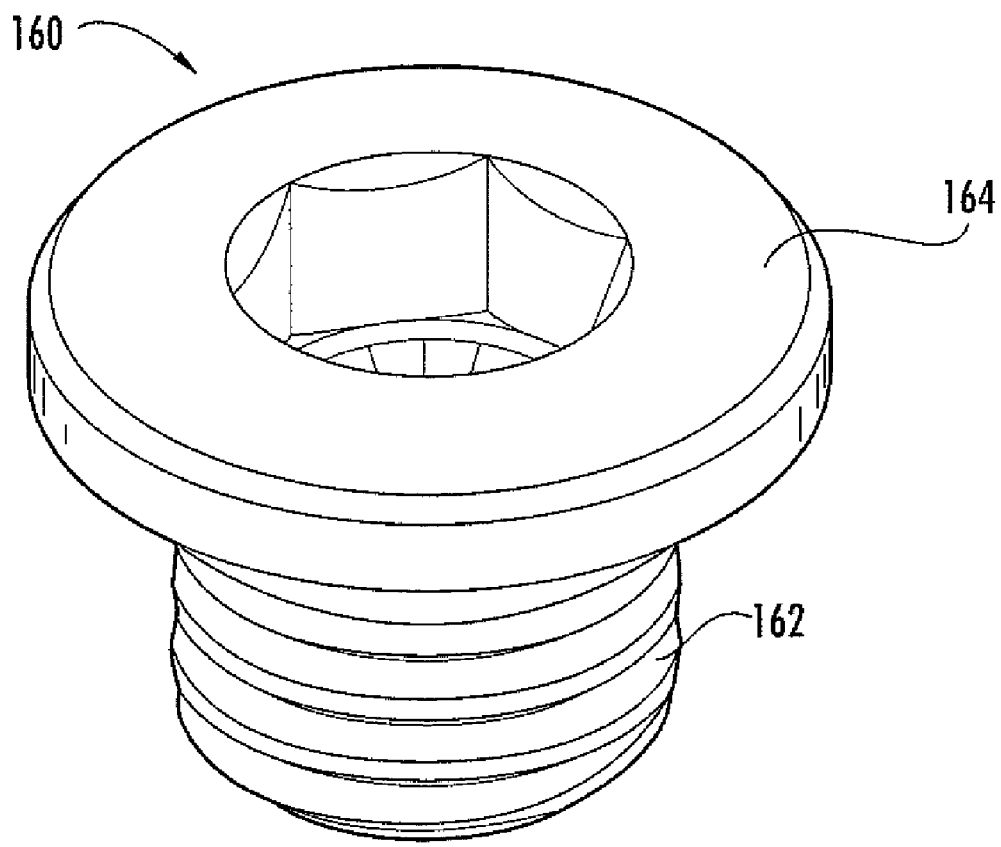
FIG. 13 is a top perspective view of a set screw with enlarged head to be used with the plate of FIG. 11.
Figure 13A:
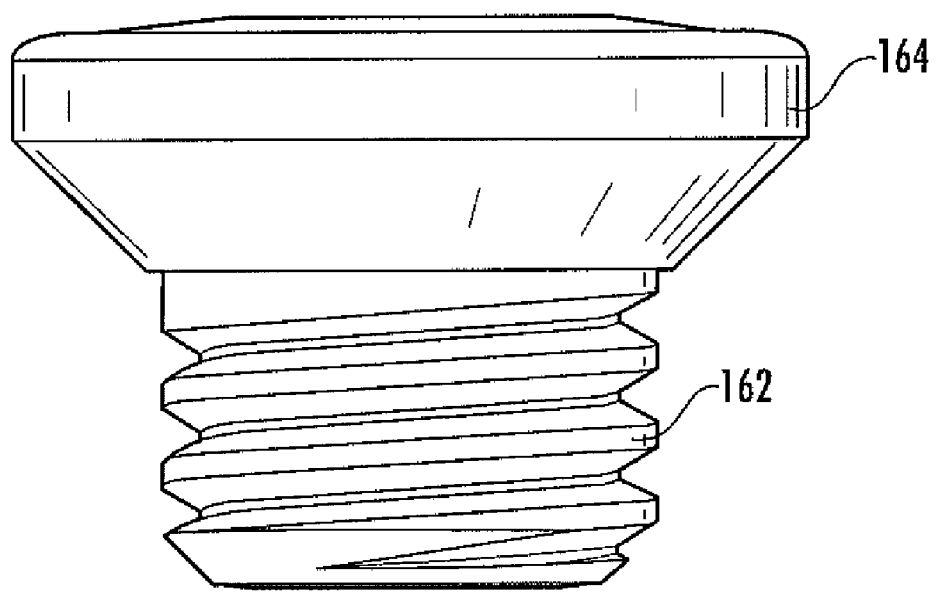
FIG. 13A is side elevation of the set screw of FIG. 13.

As may be seen in FIG. 12 (and FIG. 8, with respect to the embodiment of FIGS. 1-9), the prong bores, 134, intersect with the pockets of the bone screw holes 142. To lock the plate 104a with a plate 102, the prongs, 108 are inserted into the bores, and a large-top set screw, 160, illustrated in FIGS. 13 & 13A is inserted into the set screw hole, 152a. The top 164 of the large-top set screw has a breadth greater than that of the upper edge top, 154 of the recessed pocket for the screw. When the threads, 162 of the screw 160, engage the threads of set screw hole 152a, further rotation of the screw crushes the top 144, and bottom, 146, of the plate, locking down the prongs in the bores.

Figure 14:
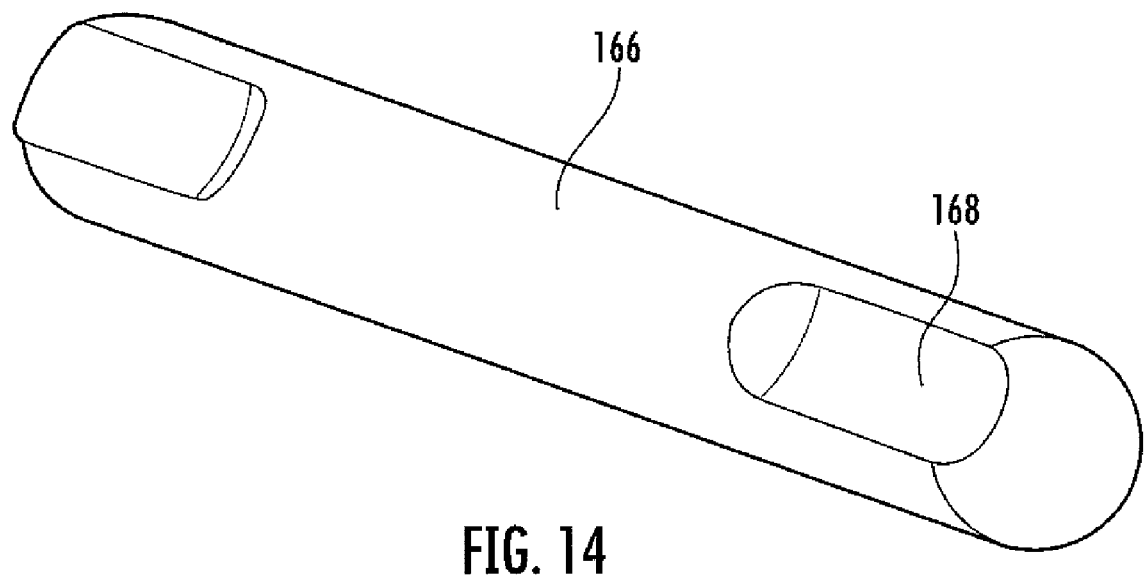
FIG. 14 is a top perspective view of a rod that may be incorporated into the bone plate of the present invention.

FIG. 14 illustrates a rod which may be used to create a pronged plate, like plate 102, from a plate with a slit and set screw holes 152a (see FIG. 11), 104a, using the locking mechanism described above. The rod, 166 may be provided with a curved surface 168, which mimics the curved surface 135 of the prongs of plate 102. Using two plates, 104a, two large-top set screws, 160 and two rods, 166, one can assemble an interlocking, adjustable length bone plate, as, for example, by placing the two prongs into the bores of one plate, 104a, and locking them in with a large-top set screw. If the prongs have the curvature, 168, they should be placed in the bores such that the curvature, 168, of the extending prongs will align with the curve of the recessed pocket for the bone screw holes, 142, once the prongs are inserted into the bores of the second plate.

The sliding bone plate the present invention may be constructed of any suitable biocompatible material, known to have sufficient structural strength and durability, such as stainless-steel, or stainless-steel alloy containing titanium, etc. One example of such a material is ASTM F-136 titanium alloy (Ti 6AL-4V). In addition the sliding bone plates of the present invention may be made of polymeric material such as PEEK (poly ethyl (ethyl-ketone)), with sufficient flex to mimic the micromotion of normal bone, to stimulate bone growth; ceramic filled biocompatible polymers, or other biocompatible materials of sufficient strength to stabilize the bone during healing, or correct a fracture of the bone.

In the preferred embodiments shown the first longitudinal plate has two prongs, however it should be understood that more than two prongs may be utilized. In the embodiment shown in FIGS. 1-9, only one threaded set screw hole, 152, is shown, and in FIG. 10, two locking holes are shown. It should be understood that the locking mechanism of the sliding bone plate of the present invention may comprise any number of threaded set screw holes, 152, for use by the surgeon. In addition, any number of bone screw holes, 114, and 142 may be provided in the first and second longitudinal plates, respectively, for use by the surgeon as he/she sees fit. Other variations on design will be obvious to those skilled in the art.

There has thus been shown and described a novel sliding bone plate which fulfills all the objects and advantages sought therefore. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

We claim:

1. A bone plate assembly having an adjustable length and comprising a first longitudinal plate having a longitudinal curvature, a lateral curvature, an upper surface and a lower surface, a first plate inner end comprising at least two spaced, straight longitudinal prongs, a first plate outer end, and disposed proximate the first plate outer end at least one bone screw aperture passing through the upper surface and the lower surface and adapted to receive a bone screw for fastening the first plate to a bone, and a second longitudinal plate having a longitudinal curvature, a lateral curvature, a length, a width, an upper plate surface and a lower plate surface, a second plate inner end comprising at least two straight longitudinal bores, each straight longitudinal bore having an inner surface extending into and terminating within the second longitudinal plate and being adapted to receive one straight longitudinal prong, a second plate outer end, and disposed proximate the second plate outer end at least one bone screw aperture passing through the upper plate surface and the lower plate surface and adapted to receive a bone screw for fastening the second plate to a bone, said straight longitudinal prongs being smoothly translatable within said straight longitudinal bores to adjust the length of the bone plate assembly, and defining an observation window between the prongs and the plates, said bone plate assembly further comprising a locking mechanism to fix the length of the bone plate assembly the locking mechanism comprising at least one threaded set screw aperture disposed between the bores, the second plate inner end and the at least one bone screw aperture of the second plate, and a set screw disposed in the at least one set screw aperture, separating the prongs and in direct contact with the prongs, wherein, when the set screw is tightened in the set screw aperture the prongs are pressed against the inner surfaces of the bores locking the prongs in place.

2. The bone plate assembly of claim 1 wherein the at least one threaded set screw aperture passes through the upper plate surface and the lower plate surface.

3. The bone plate assembly of claim 1, wherein the first and second plates have a convex upper longitudinal surface, a concave lower longitudinal surface, a convex upper lateral surface and a concave lower lateral surface.

4. The bone plate assembly of claim 1, wherein the at least one bone screw apertures of the first plate and the second plate are threaded.

5. The bone plate assembly of claim 4, wherein the at least one bone screw apertures of the first plate and the second plate are adapted for receiving bone screws for making a removeable and temporary fastening to the underlying bones.

6. The bone plate assembly of claim 1, further comprising a locking slot in the first plate outer end and a locking slot in the second plate outer end.

* * * * *